United States Patent
Jiang et al.

(10) Patent No.: US 11,000,518 B2
(45) Date of Patent: May 11, 2021

(54) USE OF COMBINATION OF VEGFR INHIBITOR AND PARP INHIBITOR IN PREPARATION OF MEDICAMENT FOR TREATING GASTRIC CANCER

(71) Applicant: Jiangsu Hengrui Medicine Co., Ltd., Jiangsu (CN)

(72) Inventors: Jiahua Jiang, Jiangsu (CN); Guoqing Cao, Jiangsu (CN); Changyong Yang, Jiangsu (CN); Lianshan Zhang, Jiangsu (CN); Jianjun Zou, Jiangsu (CN); Piaoyang Sun, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

(21) Appl. No.: 16/463,445

(22) PCT Filed: Nov. 30, 2017

(86) PCT No.: PCT/CN2017/113899
§ 371 (c)(1),
(2) Date: May 23, 2019

(87) PCT Pub. No.: WO2018/099423
PCT Pub. Date: Jun. 7, 2018

(65) Prior Publication Data
US 2019/0275021 A1 Sep. 12, 2019

(30) Foreign Application Priority Data
Dec. 1, 2016 (CN) .......................... 201611089305.X

(51) Int. Cl.
| | | |
|---|---|---|
| *A61K 31/495* | (2006.01) |
| *A61K 31/44* | (2006.01) |
| *A61K 31/335* | (2006.01) |
| *A61K 31/444* | (2006.01) |
| *A61P 35/00* | (2006.01) |
| *A61K 33/243* | (2019.01) |
| *A61K 31/337* | (2006.01) |
| *A61K 31/502* | (2006.01) |
| *A61K 45/06* | (2006.01) |
| *A61P 35/04* | (2006.01) |
| *A61K 31/497* | (2006.01) |

(52) U.S. Cl.
CPC .......... *A61K 31/444* (2013.01); *A61K 31/337* (2013.01); *A61K 31/497* (2013.01); *A61K 31/502* (2013.01); *A61K 33/243* (2019.01); *A61K 45/06* (2013.01); *A61P 35/00* (2018.01); *A61P 35/04* (2018.01)

(58) Field of Classification Search
CPC .............. A61K 31/502; A61K 31/4985; A61K 31/444; A61K 31/337
USPC .................................................. 514/250, 332
See application file for complete search history.

(56) References Cited

U.S. PATENT DOCUMENTS

| | | | |
|---|---|---|---|
| 8,362,256 B2 * | 1/2013 | Yuan .................. | A61P 43/00 546/263 |
| 9,273,052 B2 * | 3/2016 | Tang .................. | A61P 43/00 |
| 2012/0130144 A1 * | 5/2012 | Sherman ............. | A61K 31/17 600/1 |

FOREIGN PATENT DOCUMENTS

| | | |
|---|---|---|
| CN | 102307475 A | 1/2012 |
| WO | 2005/000232 A2 | 1/2005 |
| WO | 2010/031266 A1 | 3/2010 |
| WO | 2010/096627 A1 | 8/2010 |
| WO | 2012/019427 A1 | 2/2012 |
| WO | 2014/004376 A2 | 1/2014 |
| WO | 2016/116602 A1 | 7/2016 |
| WO | 2016/179123 A1 | 11/2016 |

OTHER PUBLICATIONS

Int'l Search Report dated Feb. 28, 2018 in Int'l Application No. PCT/CN2017/113899.
Zhu et al, "Current Status in Molecular Targeted Therapy against Gastric Cancer," Journal of Internal Medicine Concepts & Practice, vol. 10, No. 5, pp. 339-344 (Dec. 31, 2015).
Chen et al, "Advances of Target Therapy for Gastric Cancer," Chinese Journal of Clinical Pharmacology and Therapeutics, vol. 20, No. 8, pp. 950-955 (Aug. 31, 2015).
Zhang et al, "Novel Therapy for Advanced Gastric Cancer", World Journal of Gastrointestinal Oncology, vol. 7, No. 11, pp. 263-270 (Nov. 30, 2015).

* cited by examiner

*Primary Examiner* — Shengjun Wang
(74) *Attorney, Agent, or Firm* — Ice Miller LLP

(57) ABSTRACT

A combination of a VEGFR inhibitor and a PARP inhibitor is described. In particular, this combination can be used in the preparation of a medicament for treating gastric cancer.

5 Claims, No Drawings

USE OF COMBINATION OF VEGFR INHIBITOR AND PARP INHIBITOR IN PREPARATION OF MEDICAMENT FOR TREATING GASTRIC CANCER

CROSS-REFERENCE TO RELATED APPLICATION

This application is a Section 371 of International Application No. PCT/CN2017/113899, filed Nov. 30, 2017, which was published in the Chinese language on Dec. 1, 2016, under International Publication No. WO 2018/099423 A1, which claims priority under 35 U.S.C. § 119(b) to Chinese Patent Application No. 201611089305.X, filed on Dec. 1, 2016, the disclosures of which are incorporated herein by reference in their entireties.

FIELD OF THE INVENTION

The present invention relates to a combination of a VEGFR inhibitor and a poly(adenosine diphosphate-ribose) polymerase inhibitor, as well as a use thereof in the preparation of a medicament for treating gastric cancer.

BACKGROUND OF THE INVENTION

Gastric cancer is one of the most common malignant tumors of the digestive tract that poses a serious threat to human health. According to statistics, among all malignant tumors, the incidence of gastric cancer ranks fourth, while the mortality rate ranks third, and more than 700,000 people die of gastric cancer every year. Since the incipient symptoms are not typical, most patients with gastric cancer have reached the advanced stage at the time of treatment. The 5-year survival rate is mostly no more than 20% due to the lack of effective treatment, and the prognosis is very poor.

Vascular endothelial growth factor (VEGF) is the most important positive regulatory protein ever identified. VEGF induces phosphorylation of its receptor subtype VEGFR-2 by binding to it, and further activates a series of cascades that cause vascular endothelial cell proliferation and induce angiogenesis. Studies have shown that VEGF and its receptors are highly expressed in gastric cancer tissues, and their expression levels are positively correlated with the prognosis of gastric cancer. Therefore, the treatment of targeting VEGF or its receptors to destroy neovascularization will undoubtedly provide a novel therapeutic direction and molecular target for patients with gastric cancer. Bevacizumab is a recombinant human anti-VEGF monoclonal antibody, and is the first drug approved for anti-angiogenesis of tumor. A phase III clinical trial demonstrated that bevacizumab in combination with chemotherapy as a first-line regimen has a significant efficacy in treating advanced gastric cancer, laying the foundation for anti-gastric cancer therapy targeting neovascularization. WO2005000232A2 (publication date of Jan. 6, 2005) discloses a small molecule tyrosine kinase inhibitor Apatinib mesylate, which highly selectively competes for the ATP-binding site of VEGFR-2 in cells, blocks the downstream signal transduction, inhibits the neovascularization of tumor, and finally achieves the purpose of treating tumors. Apatinib can significantly prolong the overall survival and progression-free survival of patients with advanced gastric cancer after second-line treatment failure, and improve the control rate of the disease. Apatinib is the only oral formulation among the currently approved drugs targeting gastric cancer, and fills the gap in the third-line treatment field of advanced gastric cancer. The structure of Apatinib is shown in formula (I)

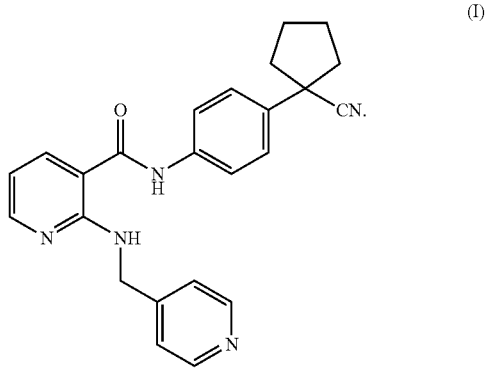 [SMILES: N#CC1(c2ccc(NC(=O)c3cccnc3NCc3ccncc3)cc2)CCCC1]

Poly(adenosine diphosphate-ribose) polymerase or poly (ADP-ribose) polymerase (PARP) plays an important role in repairing DNA single-strand break (SSB) induced by various causes. Since the FDA approved the PARP inhibitor Olaparib developed by AstraZeneca in late 2014 for treating ovarian cancer with BRCA1/2 mutation, the development of PARP inhibitors for anti-tumor treatment has developed rapidly. A number of PARP inhibitors including Niraparib, Veliparib and Rucaparib are currently in phase III clinical trials. Preclinical studies have demonstrated that in addition to being applied as a single drug, PARP inhibitors can also be used as a radiosensitizer or chemosensitizer in combination with radiotherapy or chemotherapy, so as to enhance anti-tumor efficacy and reduce the drug dose in chemotherapy or radiation dose in the radiotherapy, and reduce toxic and side effects. A recent phase II clinical trial showed that Olaparib showed an 88% response to advanced prostate cancer patients with DNA repair gene mutations, which allowed tumor growth to be inhibited or even reduced, and the overall survival was longer than the expected survival of the same type patients. Therefore, the continuous expansion of the usage mode and indication of PARP inhibitors has a good promotion for the development and application of PARP inhibitors. The occurrence and development of gastric cancer have been confirmed to be closely related to abnormal DNA damage repair function. WO2012019427A1 (publication date of Feb. 16, 2012) discloses a PARP inhibitor capable of inhibiting the growth of various tumors, and its structure is shown in formula (B)

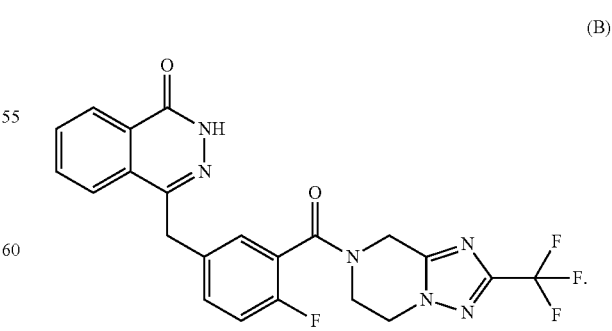

The combination of more than one anti-tumor drugs that have different targets and are interrelated is a generally accepted anti-tumor therapy, which fully utilizes the advantages of each component, and can not only improve the anti-tumor activity of each single drug but also reduce the toxicity of the drugs. A phase I clinical trial of the combination of a PARP inhibitor Olaparib and Cediranib (a drug that inhibits neovascularization by inhibiting VEGFR activity) initially demonstrated that the combination regimen is more effective than the two drugs used alone in patients with ovarian cancer, indicating that the combination regimen of the above two drugs with different targets has a good feasibility for tumor treatment.

Patent applications WO2010096627A1 (publication date of Aug. 26, 2010), WO2014004376A2 (publication date of Jan. 3, 2014), WO2016116602A1 (publication date of Jul. 28, 2016) and WO2016179123A1 (publication date of Nov. 10, 2016) disclose the use of a combination of a VEGFR inhibitor and a PARP inhibitor in treating malignant tumors (such as breast or ovarian cancer, etc). However, whether the combination has a synergy effect on the inhibition of gastric cancer or not is unknown.

SUMMARY OF THE INVENTION

The technical problem to be solved by the present invention is to provide a use of a combination of a VEGFR inhibitor and a PARP inhibitor having a synergy effect in the preparation of a medicament for treating gastric cancer.

The technical solutions of the present invention are as follows:

The present invention provide a use of a combination of a VEGFR inhibitor and a poly(adenosine diphosphate-ribose) polymerase inhibitor in the preparation of a medicament for treating gastric cancer.

Preferably, the VEGFR inhibitor is a VEGFR-2 inhibitor.

Further preferably, the VEGFR-2 inhibitor is a compound of formula (I) or a pharmaceutically acceptable salt thereof,

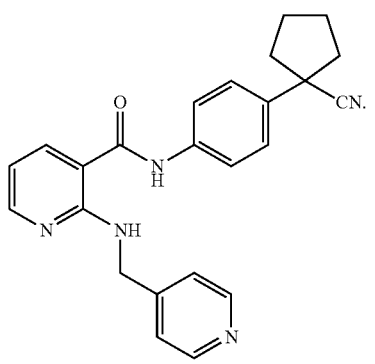

(I)

In the above embodiments, the pharmaceutically acceptable salt is selected from the group consisting of hydrochloride, mesylate, maleate, malate and besylate.

In the above embodiments, the poly(adenosine diphosphate-ribose) polymerase inhibitor is selected from the group consisting of Olaparib, Niraparib, Talazoparib, Veliparib, Rucaparib, CEP-8983 and BGB-290.

In the above embodiments, the poly(adenosine diphosphate-ribose) polymerase inhibitor is a compound of formula (B) or a pharmaceutically acceptable salt thereof,

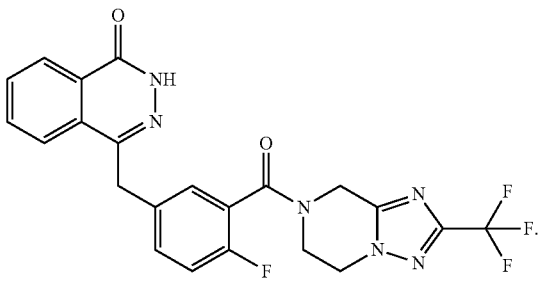

(B)

In a preferred embodiment of the present invention, the gastric cancer is selected from the group consisting of adenocarcinoma, adenosquamous carcinoma and squamous cell carcinoma.

In a preferred embodiment of the present invention, the gastric cancer is advanced gastric cancer.

Particularly preferably, the VEGFR inhibitor and the poly(adenosine diphosphate-ribose) polymerase inhibitor of the present invention are further combined with a third component, which can be selected from the group consisting of a platinum anticancer drug and a taxane anticancer drug.

In a preferred embodiment of the present invention, the platinum anticancer drug is selected from the group consisting of cisplatin, carboplatin, oxaliplatin, nedaplatin and lobaplatin.

In a preferred embodiment of the present invention, the taxane anticancer drug is selected from the group consisting of paclitaxel and docetaxel. The administration form of paclitaxel is not limited to, and can be, for example, paclitaxel injection, paclitaxel liposome or albumin-bound paclitaxel.

The combination of the present invention has a synergistic effect.

The administration mode of the combination of the present invention is selected from the group consisting of: simultaneous administration and sequential administration.

According to the use of the present invention, the VEGFR inhibitor is 0.1-1000 mg.

According to the use of the present invention, the poly (adenosine diphosphate-ribose) polymerase inhibitor is 0.1-1000 mg.

The present invention further relates to a use of a combination of a VEGFR inhibitor and a poly(adenosine diphosphate-ribose) polymerase inhibitor in the preparation of a medicament for treating gastric cancer, wherein the ratio of the VEGFR inhibitor to the poly(adenosine diphosphate-ribose) polymerase inhibitor is 0.001-1000, and preferably 1:1, 5:3 or 2:1.

The present invention further relates to a use of a combination of a VEGFR inhibitor and a poly(adenosine diphosphate-ribose) polymerase inhibitor in the preparation of a medicament for treating gastric cancer, wherein the administration dose of the VEGFR inhibitor is 1-850 mg, preferably 2.5 mg, 3 mg, 5 mg, 6 mg, 10 mg, 15 mg, 20 mg, 25 mg, 30 mg, 40 mg, 50 mg, 80 mg, 100 mg, 150 mg, 200 mg, 250 mg, 350 mg, 400 mg, 450 mg, 500 mg, 550 mg, 600 mg, 650 mg, 700 mg, 750 mg, 800 mg or 850 mg, and the administration dose of the poly(adenosine diphosphate-ribose) polymerase inhibitor is 1-500 mg, and preferably 3 mg, 6 mg, 9 mg, 10 mg, 12 mg, 15 mg, 18 mg, 20 mg, 21 mg, 24 mg, 25 mg, 27 mg, 30 mg, 33 mg, 36 mg, 40 mg, 45 mg, 60 mg, 80 mg, 100 mg, 120 mg, 150 mg, 160 mg, 200 mg, 250 mg, 270 mg, 300 mg, 350 mg, 400 mg or 450 mg.

The present invention further relates to a use of a combination of a VEGFR inhibitor and a poly(adenosine diphosphate-ribose) polymerase inhibitor in the preparation of a medicament for treating gastric cancer, wherein the VEGFR inhibitor is recommended to be administered once a day, and the poly(adenosine diphosphate-ribose) polymerase inhibitor is recommended to be administered twice a day with a 12-hour interval.

In a preferred embodiment of the present invention, it relates to a use of a combination of a VEGFR inhibitor and a poly(adenosine diphosphate-ribose) polymerase inhibitor in the preparation of a medicament for treating gastric cancer, wherein the administration dose of the poly(adenosine diphosphate-ribose) polymerase inhibitor is an escalated dose of 10 mg, 20 mg, 30 mg, 40 mg, 60 mg, 80 mg and 100 mg respectively, in combination with a fixed dose of 250 mg of VEGFR inhibitor.

In the above embodiments, the cisplatin is recommended to be administered by intravenous drip, on the first day, the eighth day, and the fifteenth day of each cycle during the continuous administration, at a fixed dose of 20 mg/m$^2$, and 1 hour after the administration of the poly(adenosine diphosphate-ribose) polymerase inhibitor and the VEGFR inhibitor, and the duration of intravenous drip should be greater than 3 hours.

In the above embodiments, the paclitaxel injection is recommended to be administered by intravenous drip, on the first day, the eighth day, and the fifteenth day of each cycle during the continuous administration, at a fixed dose of 60 mg/m$^2$, and 1 hour after the administration of the poly(adenosine diphosphate-ribose) polymerase inhibitor and the VEGFR inhibitor, and the duration of intravenous drip should be greater than 3 hours.

Significantly, the combined application of the VEGFR inhibitor and the poly(adenosine diphosphate-ribose) polymerase inhibitor of the present invention has a synergistic effect.

The present invention also relates to a pharmaceutical composition of a VEGFR inhibitor and a poly(adenosine diphosphate-ribose) polymerase inhibitor, comprising optional one or more pharmaceutically acceptable vehicles, excipients and/or diluents. The pharmaceutical composition can be formulated into any one of the pharmaceutically acceptable dosage forms. For example, the pharmaceutical formulation of the VEGFR inhibitor and the poly(adenosine diphosphate-ribose) polymerase inhibitor can be formulated into a tablet, capsule, pill, granule, solution, suspension, syrup, injection (including injection solution, sterile powder for injection and concentrated solution for injection), suppository, inhalant or spray.

In addition, the pharmaceutical composition of the present invention can also be administered to a patient or subject in need of such treatment by any suitable administration mode, for example, oral, parenteral, rectal, pulmonary or topical administration etc. When administered orally, the pharmaceutical composition can be formulated into an oral formulation, for example, an oral solid formulation such as a tablet, capsule, pill, granule and the like; or an oral liquid formulation such as an oral solution, oral suspension, syrup and the like. When formulated into an oral formulation, the pharmaceutical formulation can also comprise a suitable filler, binder, disintegrant, lubricant and the like.

The pharmaceutical composition of the VEGFR inhibitor and the poly(adenosine diphosphate-ribose) polymerase inhibitor of the present invention can be administered alone, or in combination with one or more therapeutic agents. Therefore, in certain preferred embodiments, the pharmaceutical composition also comprises one or more therapeutic agents. In certain preferred embodiments, the therapeutic agent is selected from the group consisting of: an antibody, alkylating agent, antimetabolite, antibiotic, alkaloid and hormone, wherein the alkylating agent is selected from the group consisting of bendamustine and temozolomide, the antimetabolite is selected from the group consisting of 5-fluorouracil and cytarabine, the antibody is herceptin, the antibiotic is selected from the group consisting of adriamycin and mitomycin C, the alkaloid is selected from the group consisting of vinblastine and harringtonine, and the hormone is selected from the group consisting of prednisone and thyroxine.

The components to be combined (for example, the VEGFR inhibitor and the poly(adenosine diphosphate-ribose) polymerase inhibitor as well as the second therapeutic agent) can be administered simultaneously or sequentially separately. For example, the second therapeutic agent can be administered before, at the same time of, or after the co-administration of the VEGFR inhibitor and the poly (adenosine diphosphate-ribose) polymerase inhibitor of the present invention. Moreover, the components to be combined can also be co-administered in the same formulation or in different formulations separately.

In the present invention, the term "combined administration" or "co-administration" is an administration mode, including various situations in which the two drugs are administered sequentially or simultaneously. The term "simultaneously" herein refers to the administration of the VEGFR inhibitor and the poly(adenosine diphosphate-ribose) polymerase inhibitor during the same administration cycle, for example, the two drugs are administered within two days, or within one day. The term "sequential or successive" administration includes situations in which the VEGFR inhibitor and the poly(adenosine diphosphate-ribose) polymerase inhibitor are administered respectively, in different administration cycles. These administration modes all belong to the combined administration of the present invention.

The present invention also provides a method for treating gastric cancer, comprising administering to a gastric cancer patient the aforementioned VEGFR inhibitor and poly(adenosine diphosphate-ribose) polymerase inhibitor.

The term "effective amount" of the present invention encompasses an amount sufficient to ameliorate or prevent a symptom or sign of a medical condition. The term effective amount also refers to an amount sufficient to allow or facilitate diagnosis. An effective amount for a particular patient or veterinary subject may vary depending on factors such as the condition to be treated, the general health of the patient, the route and dose of administration, and the severity of side effects. An effective amount can be the maximal dose or administration regimen that avoids significant side effects or toxic effects.

The gastric cancer patient of the present invention is preferably a patient that has received treatment failure in the first-line chemotherapy or a patient that is intolerant to the first-line chemotherapy. The first-line chemotherapy regimen should include a regimen based on platinum drugs and/or fluorouracil drugs. Moreover, the patient preferably suffers from a recurrent or metastatic gastric adenocarcinoma (including a gastroesophageal junction adenocarcinoma) according to a histological or cytological diagnosis.

Note: the definition of treatment failure: the disease is progressed during the treatment or relapsed after the treatment, and the systemic chemotherapy received must be ≥one cycle.

If not explained to the contrary, the terms in the present invention have the following meanings:

Overall survival (OS) refers to the date from a random day to the day of death caused by any reason. With respect to a subject that still survives at the last follow-up, the OS thereof is recorded as censored data by the last follow-up time. With respect to a subject that is lost to follow-up, the OS thereof is recorded as censored data by the last confirmed survival time before the loss of follow-up. The data censored OS is defined as the time from random grouping to censoring.

Objective response rate (ORR) refers to the proportion of patients whose tumor shrinks to a certain extent and remains for a certain period of time, including cases of CR and PR. The response evaluation criteria in solid tumors (RECIST 1.1 criteria) are employed to assess tumor objective response. The subjects must have measurable tumor lesions at baseline. The efficacy assessment criteria are classified into complete response (CR), partial response (PR), stable disease (SD), and progressive disease (PD) according to the RECIST 1.1 criteria.

Disease control rate (DCR) refers to the percentage of confirmed cases of complete response, partial response and stable disease (≥eight weeks) in patients with evaluable efficacy.

Quality of Life (QoL) score refers to EORTC QLQ-C30 (version 3, Chinese version). Evaluation method: the changes of related clinical symptoms and objective examination results of tumor patients before and after treatment are observed and scored, and the scores of each field of the scale are recorded in the eCRF table according to the requirements of the quality of life scale.

Complete response (CR): all target lesions disappear, and the short diameter of all pathological lymph nodes (including target nodules and non-target nodules) must be reduced to <10 mm.

Partial response (PR): the sum of target lesion diameters is reduced by at least 30% compared to the baseline level.

Progressive disease (PD): with reference to the minimum of the sum of all measured diameters of target lesions throughout the experimental study, the sum of diameters is relatively increased by at least 20% (taking as reference the baseline value if the baseline measurement is minimum); in addition, the absolute value of the sum of diameters must be increased by at least 5 mm (the appearance of one or more new lesions is also considered to be progressive disease).

Stable disease (SD): the reduction extent of target lesions does not reach the PR level, and the increase extent does not reach the PD level either, which lie between the two, and the minimum of the sum of diameters can be used as a reference during the study.

Advantageous Effects of the Present Invention

Compared with the prior art, the technical solution of the present invention has the following advantages:

(1) The combined administration of the VEGFR inhibitor and the poly(adenosine diphosphate-ribose) polymerase inhibitor of the present invention can effectively solve the problem of drug resistance and improve the efficacy of drugs.

(2) Studies have shown that the combined administration of the VEGFR inhibitor and the poly(adenosine diphosphate-ribose) polymerase inhibitor of the present invention can be used for continued treatment after first-line chemotherapy failure. The chemical stability is high, and can meet the medical needs of production, transportation and storage. The preparation process is stable, repeatable and controllable, which is suitable for industrial production.

DETAILED DESCRIPTION OF THE INVENTION

The exemplified experimental solutions for the use of the composition of the present invention in a medicament for treating gastric cancer are provided below in order to demonstrate the favorable activity and beneficial technical effects of the composition of the present invention. However, it should be understood that the following experimental solutions are provided only for the purpose of illustrating the present invention, rather than limiting the scope of the present invention. A person skilled in the art, based on the teachings in the description, can make suitable modifications or alterations to the technical solutions of the present invention without departing from the spirit and scope of the present invention.

Example 1. Efficacy of the Composition of the Present Invention on the Subcutaneous Implantation Tumor of Human Gastric Cancer PDX Model STO #069 Tumor-Bearing Nude Mice Test products: compound A (Apatinib mesylate, which can be prepared according to the method in the patent application WO2010031266A1), compound B (which can be prepared according to the method in the patent application WO2012019427A1), cisplatin (purchased from Sigma Corporation), and paclitaxel (purchased from Taizhou Crene Biotechnology Co., Ltd.).

Test animals: BALB/c nude mice, 6-7 weeks old, female, purchased from Beijing Vital River Laboratory Animal Technology Co., Ltd., with laboratory animals use license No.: SCXK (Shanghai) 2015-0022 and animal certificate No.: 11400700166108, feeding condition: SPF grade.

Control group: solvent group.

Preparation of the Solutions of Test Products:

Compound A: compound A (100 mg) was weighed, added with 0.5% carboxymethylcellulose solution (10 mL), vortex-mixed or ultrasonic-mixed until the solution was clear, and stored at 4° C., and the dose volume was 5 mL/kg;

Compound B: compound B (540 mg) was weighed and dissolved in purified water (31 mL), then added with 0.2% Tween 80 (0.18 mL) and 10% PEG 400 (9.0 mL), vortex-mixed until the solution was clear, followed by adding purified water to a solution volume of 90 mL and storing at 4° C., and the dose volume was 5 mL/kg;

Cisplatin: cisplatin (3 mg) was weighed and dissolved in normal saline (6.0 mL), the concentration of the solution was 0.5 mg/mL, and the solution was prepared to a total of 6.0 mL, stored at 4° C., and filtrated with a 0.22 μm Millipore Millex® membrane before each use;

Paclitaxel: paclitaxel (6 mg/mL, 1.5 mL) was formulated into a solution (1.5 mg/mL) with normal saline (6.0 mL) and stored at 4° C., which was freshly formulated before each use.

Tumor Model:

The patient's gastric cancer STO #069 tumor tissue (which was pathologically diagnosed as gastric poorly differentiated adenocarcinoma) was cut into small pieces (~30 mm³), and implanted subcutaneously into the right side of the nude mice. After the tumor grew to 600-700 mm³, it was passaged in the nude mice, which were defined as passage 0 (P0); after implantation of tumor passage 0 (P0), the mice were defined as passage 1 (P1); the passage was thus defined according to the order continuously implanted in nude mice; the next passage generated from FP5 was defined as FP6, and so on; and the FP6 tumor tissue was used for this study.

Experimental Procedure:

(1) Tumor implantation: the STO #069 FP6 tumor tissue (which was pathologically diagnosed as gastric poorly differentiated adenocarcinoma) was cut into small pieces (~30 mm³), and implanted subcutaneously into the right side of the nude mice. After the mean tumor size was close to 150-250 mm³, the mice were grouped and treated, a total of 7 groups, each group of 6 tumor-bearing mice. The experimental procedure for the mice was carried out according to the predetermined regimens in the experimental design of Table 1:

TABLE 1

Experimental regimens

| Group | Number of animal | Treatment | Dose | Administration mode | Administration time |
|---|---|---|---|---|---|
| 1 | 6 | 10% PEG 400 + 0.2% Tween 80/0.5% CMC | 5 mL/kg | p.o./p.o. | BID × 21/QD × 21 |
| 2 | 6 | Compound A | 50 mg/kg | p.o. | QD × 21 |
| 3 | 6 | Compound B + cisplatin | 30 mg/kg + 5 mg/kg | p.o./i.p. | BID × 21/QW × 3 |
| 4 | 6 | Compound B + paclitaxel | 30 mg/kg + 15 mg/kg | p.o./i.p. | BID × 21/QW × 3 |
| 5 | 6 | Compound A + compound B | 50 mg/kg + 30 mg/kg | p.o./p.o. | QD × 21/BID × 21 |
| 6 | 6 | Compound A + compound B + cisplatin | 50 mg/kg + 30 mg/kg + 5 mg/kg | p.o./p.o./i.p. | QD × 21/BID × 21/QW × 3 |
| 7 | 6 | Compound A + compound B + paclitaxel | 50 mg/kg + 30 mg/kg + 15 mg/kg | p.o./p.o./i.p. | QD × 21/BID × 21/QW × 3 |

Note:
p.o. refers to oral administration, i.p. refers to intraperitoneal injection, BID refers to twice a day, QD refers to once a day, and QW refers to once a week.

(2) Observation and recording: the tumor volume was measured 2-3 times per week, the mice were weighed, and the data were recorded.

(3) Tumor measurement and endpoint

The tumor volume was measured twice a week with a caliper and measured in two dimensions, the unit is $mm^3$;

TABLE 2

Efficacy of the combination of compound A, compound B, cisplatin, paclitaxel on the subcutaneous implantation tumor of human gastric cancer model STO#069 nude mice

| Group | Administration frequency | Route | Mean tumor volume ($mm^3$) (Mean ± SEM) D 0 | Mean tumor volume ($mm^3$) (Mean ± SEM) D 21 | % T/C D 21 | % tumor growth inhibition (TGI) D 21 | P value D 21 | Partial regression | Number of animals per group |
|---|---|---|---|---|---|---|---|---|---|
| Solvent | BID × 21/QD × 21 | PO/PO | 185.7 ± 18.8 | 813.6 ± 124.4 | — | — | — | 0 | 6 |
| Compound A 50 mg/kg | QD × 21 | PO | 185.4 ± 17.0 | 465.9 ± 17.0 | 44.68 | 55.32 | 0.017 | 0 | 6 |
| Compound B + cisplatin 30 mg/kg + 5 mg/kg | BID × 21/QW × 3 | PO/IP | 184.8 ± 17.4 | 427.2 ± 89.7 | 38.60 | 61.40 | 0.007 | 0 | 6 |
| Compound B + paclitaxel 30 mg/kg + 15 mg/kg | BID × 21/QW × 3 | PO/IP | 185.7 ± 15.9 | 466.2 ± 31.9 | 44.66 | 55.34 | 0.017 | 0 | 6 |
| Compound B + compound A 30 mg/kg + 50 mg/kg | BID × 21/QD × 21 | PO/PO | 185.9 ± 15.5 | 356.7 ± 47.2 | 27.21 | 72.79 | 0.001 | 0 | 6 |
| Compound A + compound B + cisplatin 50 mg/kg + 30 mg/kg + 5 mg/kg | QD × 21/BID × 21/ QW × 3 | PO/PO/IP | 185.0 ± 16.0 | 280.1 ± 37.1 | 15.14 | 84.86 | 0.000 | 0 | 6 |
| Compound A + compound B + paclitaxel 50 mg/kg + 30 mg/kg + 15 mg/kg | QD × 21/BID × 21/ QW × 3 | PO/PO/IP | 185.4 ± 15.8 | 340.2 ± 47.8 | 24.66 | 75.34 | 0.001 | 0 | 6 |

Note:
D 0: the first administration time; P value refers to the comparison with solvent using one way Anova. Number of mice at the start of the experiment: n = 6.

The tumor volume (V) was calculated as:
$V = \frac{1}{2} \times a \times b^2$, wherein a and b represented length and width, respectively.

T/C (%) = (T−T0)/(C−C0)×100%, wherein T and C represented the tumor volumes of the administration group and the solvent group at the end of the experiment, respectively; and T0 and C0 represented the tumor volumes of the administration group and the solvent group at the start of the experiment, respectively.

The endpoint of the experiment: The endpoint of the efficacy study was set to 21 days. If the tumor volume>2000 $mm^3$, or if a nude mouse lost more than 20% of its weight or was very ill and cannot get enough food or water, the nude mouse would be removed from the experimental group and euthanized.

Data Analysis:

The statistics were summarized, including mean and standard error of mean (SEM), statistical analysis of differences in tumor volume between groups, and analysis of data obtained by drug interaction that was carried out at the optimal treatment time point after the last administration (Day 21 after grouping). The tumor volume data were analyzed by One Way ANOVA, then the individual comparisons were performed using Dunnett (α=0.05), and P<0.05 was considered statistically significant.

Experimental Results:

Experimental Conclusion:

It can be seen from the experimental results that compound A alone (50 mg/kg) can inhibit the growth of subcutaneous implantation tumor of human gastric cancer STO #069 nude mice, and the tumor inhibition rate was 55.32% on Day 21 of administration. The tumor inhibition rates of the combination of compound B (30 mg/kg, BID×21) with cisplatin (5 mg/kg, QW×3), paclitaxel (15 mg/kg, QW×3) and compound A (50 mg/kg, QD×21) were 61.40%, 55.34% and 72.79% respectively, indicating that the combination of compound A with compound B is superior to compound A alone, the combination of compound B with cisplatin and the combination of compound B with paclitaxel on inhibiting tumor volume of gastric cancer cells. The three-drug combination of compound A (50 mg/kg), compound B (30 mg/kg) with cisplatin (5 mg/kg) or paclitaxel (15 mg/kg) showed a very significant anti-tumor effect, the tumor inhibition rates were 84.86% and 75.34% respectively, indicating that the effect of the three drug combinations (the combination of compound A, compound B and cisplatin, and the combination of compound A, compound B and paclitaxel) is superior to that of single drug or two-drug combination.

In summary, the combination of the VEGFR inhibitor compound A and the PARP inhibitor compound B of the present invention has a significant synergistic effect, and is significantly superior to the single VEGFR inhibitor compound A on inhibiting gastric cancer cell proliferation. Therefore, the combined application of the VEGFR inhibitor and the PARP inhibitor of the present invention has a significant inhibition effect on gastric cancer cell. The further combination with cisplatin or paclitaxel, i.e., the three-drug combination, is more superior to single drug or two-drug combination.

Example 2. Efficacy and Safety of the Composition of the Present Invention for Treating Gastric Cancer The phase I clinical trial (NCT03026881) enrolled ten subjects who had received treatment failure in the first-line chemotherapy or were intolerant to the first-line chemotherapy. The first-line chemotherapy regimen should include a regimen based on platinum drugs and/or fluorouracil drugs. Moreover, the patients suffered from a recurrent or metastatic gastric adenocarcinoma (including a gastroesophageal junction adenocarcinoma) according to a histological or cytological diagnosis.

Note: the definition of treatment failure: the disease is progressed during the treatment or relapsed after the treatment, and the systemic chemotherapy received must be ≥one cycle.

Administration Regimen:
Compound A: the initial dose was 250 mg, orally administrated, once a day;
Compound B: the initial dose was 20 mg, 30 mg or 40 mg, twice a day; if the first efficacy evaluation (including imaging and serological examination) was evaluated by the investigator and was considered to be not effectively relieved, and no adverse events of grade 3 or above occurred during the administration, the dose can be increased with the consent of the subject.
Paclitaxel: intravenous injection
Data Collection:
The efficacy data collection is shown in Table 3.

TABLE 3

| Compound B Dose group | Days of the combination | Imaging evaluation | | | | |
|---|---|---|---|---|---|---|
| | | C2D1 | C3D1 | C5D1 | C7D1 | C9D1 |
| 20 mg | 257 | PR | PR | PR | PR | PR |
| | 215 | SD | SD | SD | SD | |
| | 187 | PR | PR | PR | | |
| | 56 | SD | PD | | | |
| 30 mg | 152 | SD | SD | SD | | |
| | 56 | SD | PD | | | |
| | 109 | SD | SD | | | |
| | 70 | SD | PR | | | |
| | 56 | SD | PR | | | |
| | 39 | PR | | | | |

Note:
C2D1 refers to Day 1 of Cycle 2

It can be seen from the data of ten clinical cases that the partial response (PR) of the subject's disease is 50%. In Cycle 2, the stable disease (SD) of the subject is 37.5% and the disease control rate (DCR) is up to 87.5%.

Adverse events occurred mostly in hematological toxicity, including leukopenia, neutropenia and hemoglobin reduction etc. The hypophosphatemia adverse event occurred in only one case (grade 3) in the 30 mg dose group.

What is claimed is:

1. A method for treating gastric cancer in a subject in need thereof comprising administering to the subject a combination of a VEGFR inhibitor, a poly(adenosine diphosphate-ribose) polymerase inhibitor, and paclitaxel, wherein the VEGFR inhibitor is a compound of formula (I) or a pharmaceutically acceptable salt thereof, and the poly(adenosine diphosphate-ribose) polymerase inhibitor is a compound of formula (B) or a pharmaceutically acceptable salt thereof:

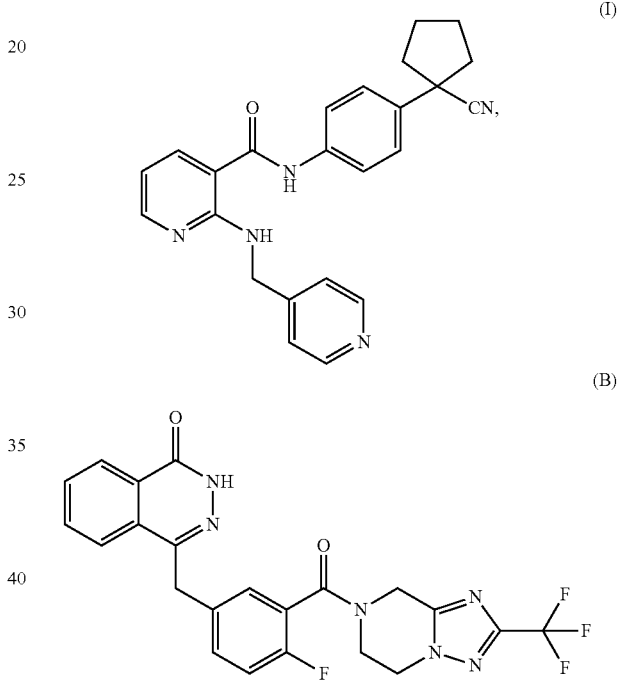

wherein the administration dose of the poly(adenosine diphosphate-ribose) polymerase inhibitor is selected from 20 mg, 30 mg, and 40 mg, twice a day, the administration dose of the VEGFR inhibitor is 250 mg, once a day, and the administration dose of paclitaxel is 60 mg/m$^2$, once a week.

2. The method according to claim 1, wherein the pharmaceutically acceptable salt is selected from the group consisting of hydrochloride, mesylate, maleate, malate and besylate.

3. The method according to claim 1, wherein the gastric cancer is selected from the group consisting of adenocarcinoma, adenosquamous carcinoma and squamous cell carcinoma.

4. The method according to claim 1, wherein the gastric cancer is an advanced gastric cancer.

5. The method according to claim 1, wherein the combination has a synergistic effect.

* * * * *